United States Patent [19]

Scheubeck et al.

[11] 4,279,727
[45] Jul. 21, 1981

[54] DEVICE FOR MEASURING THE EMISSION OF GASEOUS INORGANIC FLUORINE OR CHLORINE COMPOUNDS

[75] Inventors: Egmont Scheubeck; Gertrud Blazevic; Marianne Boehner, all of Erlangen, Fed. Rep. of Germany

[73] Assignee: Siemens Aktiengesellschaft, Munich, Fed. Rep. of Germany

[21] Appl. No.: 105,217

[22] Filed: Dec. 19, 1979

[30] Foreign Application Priority Data

Dec. 28, 1978 [DE] Fed. Rep. of Germany ....... 2856490

[51] Int. Cl.$^3$ ............................................ G01N 27/26
[52] U.S. Cl. ................................ 204/195 R; 204/1 T
[58] Field of Search .............. 204/195 M, 195 R, 1 B; 3/23

[56] References Cited

U.S. PATENT DOCUMENTS 3,058,901  10/1962  Farrah ................................. 204/1 B Primary Examiner—Howard S. Williams
Attorney, Agent, or Firm—Kenyon & Kenyon

[57] ABSTRACT

The invention relates to a device for measuring the emission of gaseous inorganic fluorine or chlorine compounds in exhaust gases by drawing the exhaust gases into a bulb-shaped absorption vessel containing a flowing-through absorption liquid and a cylindrical liquid separator and a cylindrical continuous-flow measuring cell with a fluorine-ion-sensitive or chlorine-ion-sensitive electrode measuring means for the potentiometric determination of the fluorine or chlorine-ion concentration. The absorption vessel is secured on a plate above the continuous flow measuring cell and the liquid separator is situated in between.

4 Claims, 5 Drawing Figures

DEVICE FOR MEASURING THE EMISSION OF GASEOUS INORGANIC FLUORINE OR CHLORINE COMPOUNDS

BACKGROUND OF THE INVENTION

The invention relates to a device for measuring the emission of gaseous inorganic fluorine or chlorine compounds, wherein the exhaust gas to be examined is drawn into the device, through a heated sampling probe, by means of pumps into an absorption liquid and a liquid separator, and wherein the device comprises a fluorine-ion-sensitive or chlorine-ion-sensitive electrode measuring chain or sequence for measuring the fluorine ion or chlorine ion concentration.

The devices used heretofore for determining gaseous inorganic fluorine or chlorine compounds, for example, in garbage incinerators, work with intermittent (batchwise) photometric or potentiometric determination of the measurement values (ANALYTICAL CHEMISTRY, vol. 40, No. 11 (1968), pages 1658 to 1661). The earliest indication of the measured value takes place only every 5 minutes and generally, every 20 to 30 minutes. These known devices do not meet the requirements of industrial plants, where reliable and accurate analysis results are required automatically and the determination of the noxious substances and the readout of the measured values should be continuous as far as possible. Also, the sampling probe in the known device is matched to the specific plant where it is installed and, in particular, no safe, loss-free transfer to the measuring cell is possible, particularly for hydrofluoric acid. Also, relatively long adjustment times up to constant end potential are required.

SUMMARY OF THE INVENTION

It is an object of the present invention to provide a device which has none of the noted disadvantages of the known devices. The objective is in particular to ensure with simple design and reliable means automatic and continuous determination, with continuous measured-value read-out via recorders, printers and the like, of emitted inorganic, gaseous fluorine or chlorine compounds.

The solution to this problem comprises a device for measuring the emission of gaseous inorganic fluorine or chlorine compounds, comprising means for drawing exhaust gas to be analyzed into the device, receiving means within said device for receiving said exhaust gas and for receiving a liquid for absorbing the inorganic fluorine or chlorine compounds in said gas, separating means for separating the liquid containing absorbed inorganic fluorine or chlorine compounds from gas, means for measuring quantities of said fluorine or chlorine compounds in said liquid, and value means for directing the flow of said liquid and liquid or liquids used for calibration of said device, said receiving, separating, measuring and valve means being affixed in relative positions on a base or plate such that said receiving means is positioned vertically above said measuring means and said separating means is positioned intermediate said receiving and measuring means.

BRIEF DESCRIPTION OF THE DRAWINGS

There is shown in the figures.

DETAILED DESCRIPTION OF THE INVENTION

Figure 1:
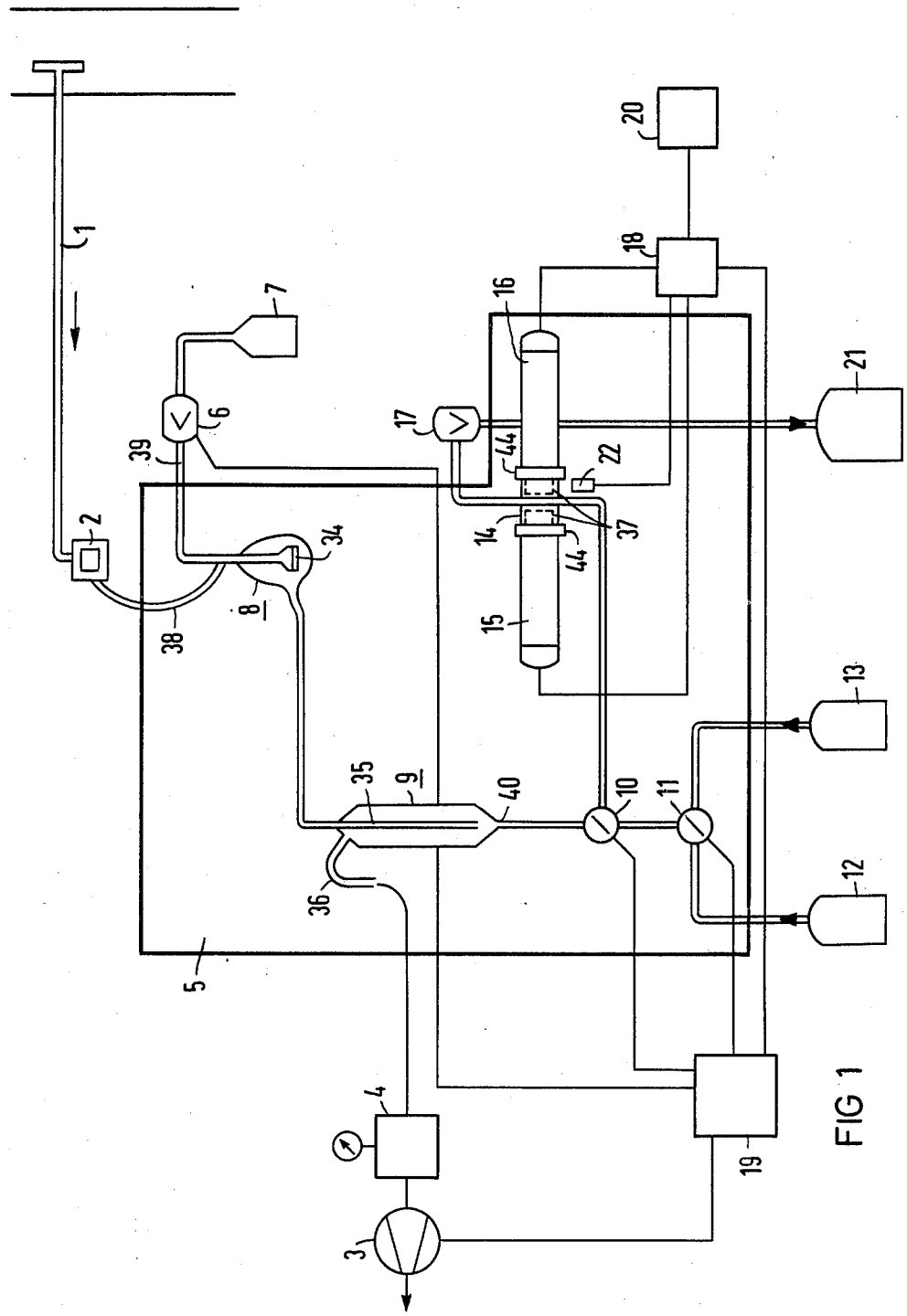
FIG. 1, a schematic diagram of the device,
FIG. 2, an absorption vessel in cross section, according to FIG. 1,
FIG. 3, a liquid separator in a cross section, according to FIG. 1,
FIG. 4, an electrode mount with seals according to FIG. 1, and in
FIG. 5, a measuring cell in a cross section, according to FIG. 1.
Figure 2:
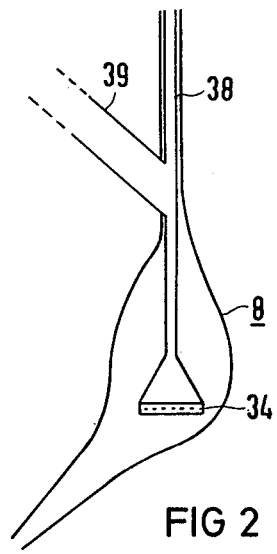
Figure 3:
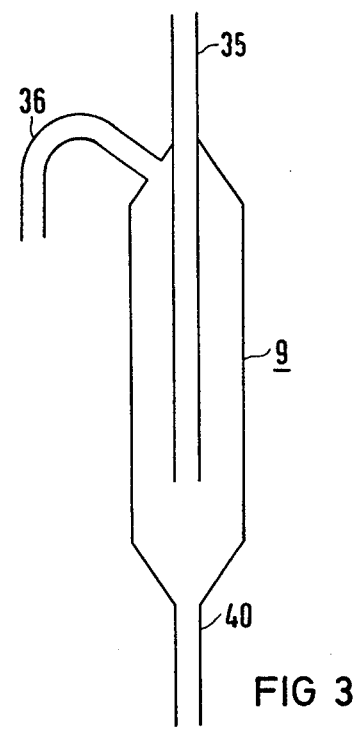
Figure 4:
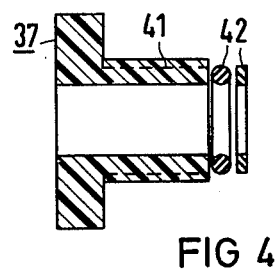
Figure 5:
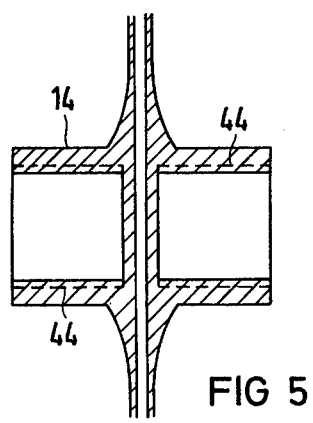

With reference to the figures, the device of the present invention is characterized, in its particulars, by a bulb-shaped absorption vessel 8 receiving the drawn-in exhaust gases in the drawn-in absorption liquid 7; a cylinderical liquid-separator 9 and a cylindrical continuous-flow measuring cell 14, which are arranged so that the absorption vessel 8 is secured on a plate 5 above the continuous-flow measuring cells 14 with the liquid separator 9 situated in between, and the magnetic valves 10 and 11 also being affixed on the plate 5. The device is provided with a provision for self-calibration with standard solutions. The sampling probe is flexible and heatable and is provided with a chemically stable lining, preferably of gold or platinum. The gas sampling, concentration determination and measured-value readout take place continuously. Maintenance-free and uninterrupted operation of the equipment is possible for a period of about 7 days. Response times of about 35 seconds are readily attainable.

The bulb-shaped absorption vessel 8 can contain a frit 34. If a gas sample and absorption solution are passed through, the frit brings about intensive mixing for the quantitative absorption of the fluorine or chlorine compounds to be determined in the absorption solution. The sample gas is fed via 38 laterally into the feed line 39 for the absorption solution 7 above the outlet through the frit; the discharge takes place to one side at the bottom via a funnel-shaped outlet. Teflon plugs 37 with thread 41 and a combined seal 42 each have been found to be particularly practical for fastening the electrodes in the continuous-flow measuring cell 14.

In the cylindrical liquid separator 9, it has been found to be advantageous to conduct the absorption liquid containing sample gas via a straight inlet tube 35 close to the liquid outlet 40 in such a manner that it can emerge drop by drop. The escaping gas is discharged at the lateral upper end of the liquid separator via a bent tube 36.

A cylindrical glass vessel with 2 mm inside diameter and two threaded stubs 44 for receiving the teflon plugs has been found to be advantageous for fastening the electrodes.

For determining analytically the emitted quantities of gaseous inorganic fluorine or chlorine compounds, the exhaust gas or the exhaust gas sample is drawn via a heated, flexible sampling probe, by means of a gas metering pump, into a suitable bulb-shaped absorption vessel containing continuously fedin absorption liquid. After the gaseous fluorine or chlorine compounds have been absorbed from the exhaust gas, the liquid is degassed in a cylindrical liquid separator. The absorption solution containing the fluorine or the chlorine ions is drawn by a liquid pump into a cylindrical continuous-flow measuring cell of small volume, where the potentiometric determination of the fluorine-or chlorine-ion concentration takes place by means of a fluorine-ion-sensitive or chlorine-ion-sensitive electrode measuring chain. Subsequently, the solution flows into the waste water tank.

The device shown in FIG. 1 shows a gas pump 3. The gas sample is drawn through the pump and the gas regulating system 4, via a heatable sampling probe 1 and filter 2, through the bulb-shaped absorption vessel 8 via the lateral feed line 38. At the same time, absorption solution 7 is transported through the feed line 39 by means of the liquid pump 6. The now fluoride-containing solution is then drawn by the second liquid pump 17 from the cylindrical liquid separator 9 through the cylindrical continuous flow measuring cell 14 with the fluorine-ion-sensitive indicator electrode 15 and the reference electrode 16. The absorption vessel 8, the liquid separator 9 and the continuous-flow measuring cell 14 form a unit by means of a short hose or tube connections and are fastened, together with the magnetic valves 10 and 11, on a plate 5. The electrode potential is amplified linearly via the amplifier 18 and registered on the recorder 20. The waste water is conducted into the tanke 21. A temperature sensor 22 serves for compensating the temperature effect on the measured value. Calibration can be performed automatically after a measuring cycle taking 52 minutes; the time calibration can be selected. The calibration takes 8 minutes. By appropriately switching the magnetic valves 10 and 11, calibration solution I is first drawn through the measuring cell 14 from 12 and then, calibration solution II from 13. If deviations of the electrode potential from the set value occur, the amplifier 18 is automatically recalibrated by the control 19.

The pump 3 for the gas sampling and the pump 6 for the absorption solution are automatically switched off during the calibration cycle.

In a similar manner, chlorine can be determined analytically from gaseous inorganic chlorine compounds, using a chlorine-ion-sensitive indicator electrode, the gas sampling, concentration determination and measured-value readout taking place continuously.

What is claimed is:

1. A device for continuously measuring the emission of gaseous inorganic fluorine or chlorine compounds, comprising means for continuously drawing exhaust gas to be analyzed into the device, receiving means within said device for continuously receiving said exhaust gas and for receiving a liquid for absorbing the inorganic fluorine or chlorine compounds in said gas, separating means for continuously separating the liquid containing absorbed inorganic fluorine or chlorine compounds from gas, means for continuously, directly measuring quantities of said fluorine or clorine compounds in said liquid by potentiometric methods and valve means for directing the flow of said liquid and liquid or liquids used for calibration of said device, said receiving, separating, measuring and valve means being affixed in relative positions on a base or plate such that said receiving means is positioned vertically above said measuring means and said separating means is positioned intermediate said receiving and measuring means.

2. The device of claim 1 wherein said receiving means contains means for bringing about intensive mixing between the exhaust gas and the absorption liquid.

3. The device of claim 1 wherein said measuring means comprises a fluorine or chlorine-ion sensitive indicator electrode and a reference electrode.

4. The device of claim 1 wherein said separating means contains an inlet tube for receiving said mixture of gas and absorption liquid which tube extends closely ahead of the outlet opening of said separating means.

* * * * *